(12) United States Patent
Lucas (10) Patent No.: US 11,246,809 B2
(45) Date of Patent: Feb. 15, 2022

(54) COMPOSITION

(71) Applicant: GlaxoSmithKline Consumer Healthcare (UK) IP Limited, Middlesex (GB)

(72) Inventor: Robert Anthony Lucas, Weybridge (GB)

(73) Assignee: GlaxosSmithKline Consumer Healthcare (UK) IP Limited, Middlesex (GB)

( * ) Notice: Subject to any disclaimer, the term of this patent is extended or adjusted under 35 U.S.C. 154(b) by 0 days.

(21) Appl. No.: 16/652,538

(22) PCT Filed: Oct. 1, 2018

(86) PCT No.: PCT/EP2018/076560
§ 371 (c)(1),
(2) Date: Mar. 31, 2020

(87) PCT Pub. No.: WO2019/068596
PCT Pub. Date: Apr. 11, 2019

(65) Prior Publication Data
US 2020/0237625 A1 Jul. 30, 2020

(30) Foreign Application Priority Data
Oct. 2, 2017 (GB) .................................. 1715949

(51) Int. Cl.
| A61K 8/02 | (2006.01) |
| A61K 8/04 | (2006.01) |
| A61K 8/21 | (2006.01) |
| A61K 8/24 | (2006.01) |
| A61K 8/25 | (2006.01) |
| A61Q 11/00 | (2006.01) |

(52) U.S. Cl.
CPC .............. *A61K 8/025* (2013.01); *A61K 8/042* (2013.01); *A61K 8/21* (2013.01); *A61K 8/24* (2013.01); *A61K 8/25* (2013.01); *A61Q 11/00* (2013.01); *A61K 2800/28* (2013.01); *A61K 2800/412* (2013.01)

(58) Field of Classification Search
None
See application file for complete search history.

(56) References Cited

U.S. PATENT DOCUMENTS

| 4,528,181 A | 7/1985 | Morton et al. |
| 4,562,063 A | 12/1985 | Hayes et al. |
| 2006/0110338 A1 | 5/2006 | McGill et al. |
| 2010/0203092 A1 | 8/2010 | Ley et al. |
| 2016/0106640 A1 | 4/2016 | Brown et al. |
| 2020/0109056 A1* | 4/2020 | Gallis ................... C01B 33/193 |

FOREIGN PATENT DOCUMENTS

| EP | 0 216 278 A2 | 4/1987 |
| JP | 2006 306841 A | 11/2006 |

* cited by examiner

*Primary Examiner* — Nannette Holloman
(74) *Attorney, Agent, or Firm* — Roshni A. Sitapara (57) ABSTRACT

The present invention relates to dentifrice compositions comprising spherical, anhydrous, amorphous, silica gel particles having a pore volume of less than 0.1 ml/g and an orally acceptable carrier. Such compositions can effectively clean, polish and remove stains from the surface of teeth or dentures without a high degree of abrasion thereby reducing scratching and damage to the tooth or denture surface. Such compositions thereby provide superior cleaning, polishing, gentle stain removal and whitening of tooth surfaces or dentures.

11 Claims, 7 Drawing Sheets

Figure 1: Stained pellicle removal values for various dentifrice formulations

Figure 2: Relative dentine abrasivity values of various dentifrice formulations

Values connected by letters a, b or c do not differ significantly ($p>0.05$) as determined by Student Newman-Keuls analysis.

Figure 3: SEM images of silica samples at low and high magnification showing the particle size and morphology

| Sample | Low magnification (X 2000) | High magnification (X 8000) |
|---|---|---|
| Zeodent 103<br><br>Irregular aggregates |  |  |
| Zeodent 113<br><br>Irregular aggregates |  |  |
| Sunsphere NP-30<br><br>Spheres of ~1-10μm in diameter |  |  |
| Sample | Low magnification (X 2000) | High magnification (X 8000) |
| Spheron N2000J<br>Spheres of ~0.5-20μm in diameter |  |  |

Figure 3 CONT.

| | | |
|---|---|---|
| Spheron P-1500 Spheres with rough surfaces of ~0.5-20μm diameter | | |
| Teco-Sil 44C Irregular particles and plates | | |
| Teco-Sil 44CSS Irregular particles and plates | | |

Figures 4A-4E: Adsorption / Desorption Isotherms (by Belsorp – mini)

Figure: 5A-Pore Distribution (Desorption):

Fig 5A: FB- 3SDC                    Fig.5B: FB-5SDC

Fig.5C : ADMAFINE FE975a

Fig.5D ADMAFINE SC5500-SQ

Fig.5E: NP-30

COMPOSITION

This application is a 371 of International Application No. PCT/EP2018/076560, filed Oct. 1, 2018, which claims the priority of GB Application No. 1715949.2 filed Oct. 2, 2017, which is incorporated herein in its entirety.

FIELD OF THE INVENTION

The present invention relates to dentifrice compositions comprising spherical, anhydrous, amorphous silica gel particles having a pore volume of less than 0.1 ml/g and an orally acceptable carrier. Such compositions can effectively clean, polish and remove stains from the surface of teeth or dentures without a high degree of abrasion thereby reducing scratching and damage to the tooth or denture surface. Such compositions thereby provide superior cleaning, polishing, gentle stain removal and whitening of tooth surfaces or dentures.

BACKGROUND OF THE INVENTION

Oral care compositions, in particular dentifrices, are used to clean teeth on a daily basis. Dentifrices will aid in the removal of food particles and tooth discolouration caused by substances such as tobacco, tea or wine in addition to the removal of plaque and other soft materials from the tooth. Cleaning and polishing the tooth surfaces is affected by either chemical processes such as materials that bind to elements within plaque or by mechanical means such as abrasive substances.

Dentifrices commonly incorporate an abrasive material for mechanical cleaning and polishing of teeth by abrading deposits. The abrasive material is primarily intended to effect mechanical removal of deposits from the surface of teeth, e.g. by removal of the pellicle film and plaque adhered to the tooth surface. The plaque and pellicle film is prone to discolouration and staining for example by comestibles such as tea and coffee and by tobacco, resulting in unsightly appearance of the teeth. While such mechanical removal is important for effecting cleaning, it is vital that the abrasive used is not unduly harsh in order to minimise damage to the tooth surface. In addition to cleaning and polishing the teeth, white teeth have long been considered cosmetically desirable.

Japanese Laid-open Patent Application (Kokai) No. 87,507/1987 (JPS6287507) discloses a dentifrice comprising fine spherical silica gel particles. The particles exhibit a specific surface area of 50-1200 $m^2/g$, preferably 200-1000 $m^2/g$ as determined by the Brunauer Emmett-Teller (BET) method; a pore volume of 4.0 ml/g or less, preferably 0.1-1.5 ml/g; a refractive index of 1.40-1.48, a mean particle size of 30 microns ($\mu$) or less and a moisture content of 65% or less, preferably 45%, and a particle size distribution of 2-50$\mu$. According to JPA (Kokai) No. 87,507/1987, by controlling the physical properties in the ranges described above, the abrasive performance can be ranged from high to low. The fine spherical silica gel particles can be prepared by one of two methods: a first method wherein a silica hydrosol, having a pre-adjusted pH, is suspended in a non-affinity oil-like medium, solidified in the suspension, washed to remove impurities and then dried, and a second method wherein the silica hydrosol is sprayed in air to form a gel, which is then washed to remove impurities and dried. The exemplified dentifrice compositions (Examples 1-5) comprise from 15.0 to 40.0% by weight of a fine silica gel material. Further the fine silica gel material used in the Examples is disclosed as having the following physical properties: a specific surface area ($m^2/g$) ranging from 443 to 763; a pore volume (ml/g) from 0.46 to 0.61; a refractive index of 1.467; an average particle size ($\mu$) from 5.8 to 8.6 and a moisture content (%) from 1.0 to 2.0.

AU-A-55125/94 (Johnson & Johnson Consumer Products Inc) discloses a dentifrice composition comprising 0.01-5 wt. % of a carboxyvinyl polymer and less than 15 wt. % of a spherical silica. According to AU-A-55125/94, use of 40-15% spherical silica gel fine particles (as described in JPA (Kokai) No. 87,507/1987) in a gel-like dentifrice containing 50% or more of water, is likely to damage teeth due to high abrasion. Further, according to AU-A-55125/94, when the dentifrices (as described in JPA (Kokai) No. 87,507/1987) are used together with an electric toothbrush, the abrasive is liable to scatter and soil the user's clothing. Still further, owing to the large amount of abrasive used, the dentifrice feels rough in the mouth and does not provide the consumer with a pleasant mouthfeel experience. These problems are solved according to AU-A-55125/94 by the provision of a dentifrice composition comprising less than 15 wt % of a spherical silica gel of a specific form having specific properties and a carboxyvinyl polymer. The properties referred to include a specific surface area measured by a BET method of 550-750 $m^2/g$, a pore volume of 0.5-1.2 ml, a water content after drying at 180° C. for 2 hours of 5.0% or less, an average particle size measured by a Coulter counter of 5.0$\mu$ or less, and a pH of an aqueous slurry in a concentration of 5% of 7.0-6.0.

US 2010/0203092 A1 (Ley et al.) discloses a dental, particularly a remineralizing, composition comprising spherical, non-porous dental particles having a particle size between 0.1$\mu$ and 2$\mu$ made of silica gel in a one-part combination, comprising at least one combination agent, and wherein the dental particles are present in an amount such that the $SiO_2$ amount resulting from the silica gel is less than 1 wt. %. The invention is disclosed as providing dental compositions and particles which on the one hand can penetrate the tooth surface sufficiently to efficiently contribute to the remineralization of the tooth structure of enamel and dentin and/or on the other hand facilitate an obstruction of transport of matter and transmission of signals within the tubules and a subsequent desensitization of the teeth by remineralization and crystal growth within the pores of the enamel as well as in dentin tubules and by blocking the tubules.

WO2010/068433 (The Procter & Gamble Company) and related applications discloses oral care compositions comprising a fused silica (which is disclosed, for some types, as having a CAS # of 60676-86-0). In contrast to a silica gel material, a fused silica is typically produced by melting high purity silica sand at very high temperatures at around 2000° C. or even higher such as around 4000° C. The process of heating silica to such high temperatures is said to destroy the porosity and surface functionality of the silica and to result in a low BET surface area i.e. in the range from 1 $m^2/g$ to 50 $m^2/g$. Fused silica, according to WO2010/068433 and relative to other types of silica, has a low amount of free or/and bound water, typically less than 10%.

U.S. Pat. No. 8,734,764 B2 (Sunstar Inc.) discloses an oral composition comprising a fused silica and a dental abrasive. According to U.S. Pat. No. 8,734,764 the oral composition therein has a high stain removal ability relative to its abrasive ability thereby making it possible to efficiently remove stains without damaging the teeth more than necessary. The fused silica can be produced by fusing silicon dioxide powder by flames of high temperatures (for example 2,000 to 3,000° C.) or by oxidizing and dissolving silicon powder or cyclic siloxane by high temperature flames. According to U.S. Pat. No. 8,734,764 since the silica is fused once and solidified, the silica particles have a high density and an increased hardness. The fused silica particles are disclosed as preferably having a high degree of sphericity i.e. their shape is close to a complete sphere. BET specific surface area of the fused silica is disclosed as 15 m$^2$/g or less, preferably 10 or less. Oil absorption is disclosed as usually 20 mL/100 g or less, preferably 10 mL/100 g.

SUMMARY OF THE INVENTION

In a first aspect the present invention, relates to a dentifrice composition comprising spherical, anhydrous, amorphous silica gel particles having a pore volume of less than 0.1 ml/g and an orally acceptable carrier. The silica gel referred to herein is not a fused silica as described in WO2010/068433 or U.S. Pat. No. 8,734,764 B2. A "fused" silica involves a "fusing" step in its process of manufacture. The silica gel particles of use in the present invention are non-fused. Such particles may be obtained by a process that involves precipitation followed by calcination (i.e. heating to a high temperature but below the melting or fusing point) to remove water to produce a dense (low porosity or non-porous) particulate silica material. An example of such a process is described in U.S. Pat. No. 7,070,748 B2.

In one aspect the present invention provides a dentifrice composition comprising spherical, anhydrous, amorphous silica gel particles wherein the silica gel particles comprise a pore volume of less than 0.1 ml/g such as from 0.03 ml/g to 0.07 ml/g; a mean particle diameter from 1µ to 10µ; an oil absorption capacity of 20 ml/100 g to 50 ml/100 g; and a BET surface area of 50 m$^2$/g or less.

The present invention is based upon the discovery that particular silica gel particles, as described herein, exhibit surprisingly good cleaning properties without being unduly abrasive as compared to other silicas (both precipitated and fused silicas). It has been found that stains can be removed in a highly efficient manner, for example by brushing teeth using a dentifrice composition comprising silica gel particles having the properties as described herein. Further the composition does not suffer from unacceptably high enamel or dentine abrasion which would otherwise render the composition unsuitable for use as a consumer healthcare product, intended for use on a daily basis.

DETAILED DESCRIPTION OF THE INVENTION

The present invention is described in more detail below.

The following definitions should be considered in reviewing the description of the invention as set forth below.

As used herein, the word "comprising" encompasses "consisting of" and "consisting essentially of".

As used herein, the word "include", and its variants, is intended to be non-limiting such that recitation of items in a list is not to the exclusion of other items that may also be useful in the materials, compositions and methods of the invention.

All percentages used herein are by weight of the total dentifrice composition, unless otherwise specified.

As used throughout, ranges are used as a shorthand for describing each and every value that is within the range. Any value within the range can be selected as the terminus of the range.

Herein, "effective amount" means an amount of a given agent or material sufficient to provide a positive benefit, usually an oral health benefit.

As used herein, the word "about", when applied to a value for a parameter of a composition indicates that the calculation or measurement of the value allows some slight imprecision without having a substantial effect on the chemical or physical attributes of the composition.

A dentifrice composition is a product that is intended for application to the oral cavity for a period of time sufficient to contact all of the tooth surfaces and/or oral tissues for purposes of oral activity. As used herein, a "dentifrice composition" means a paste or gel formulation unless otherwise specified.

Silica gel particles of use in the invention are available commercially from Asahi Glass SI-Tech. Co., Ltd., 13-1, Kitaminatomachi, Wakamatsu-ku, Fukuoka, 808-0027, Japan. and are sold under the brand name Sunsphere®, for example Sunsphere NP-30 and Sunsphere NP-100. A CAS # for some types of silica gel particles of use in the invention is 7631-86-9. Sunsphere® silica gel particles are derived from sodium silicate and contain no crystalline silica. They consist of spherical particles of almost identical size which do not cohere and which provide a smooth texture. Sunsphere® silica gel particles are known for use in the cosmetics skincare industry e.g. for use in foundations and makeup. They are also known for use in the paint industry as resin fillers to provide smoother surfaces, improved fluidity, film anti-blocking effects and moisture adsorption properties. In one embodiment the silica gel particles of use in the invention comprise a combination of the following indicated properties or thereabouts (±10%):

| Property | NP-30 | NP-100 |
|---|---|---|
| Mean particle size (µm) | 4 | 10 |
| Specific surface area (m$^2$/g) | 40 | 50 |
| Pore volume (ml) | 0.05 | 0.1 |
| Oil absorption (ml/100 g) | 30 | 35 |

Figure 3:
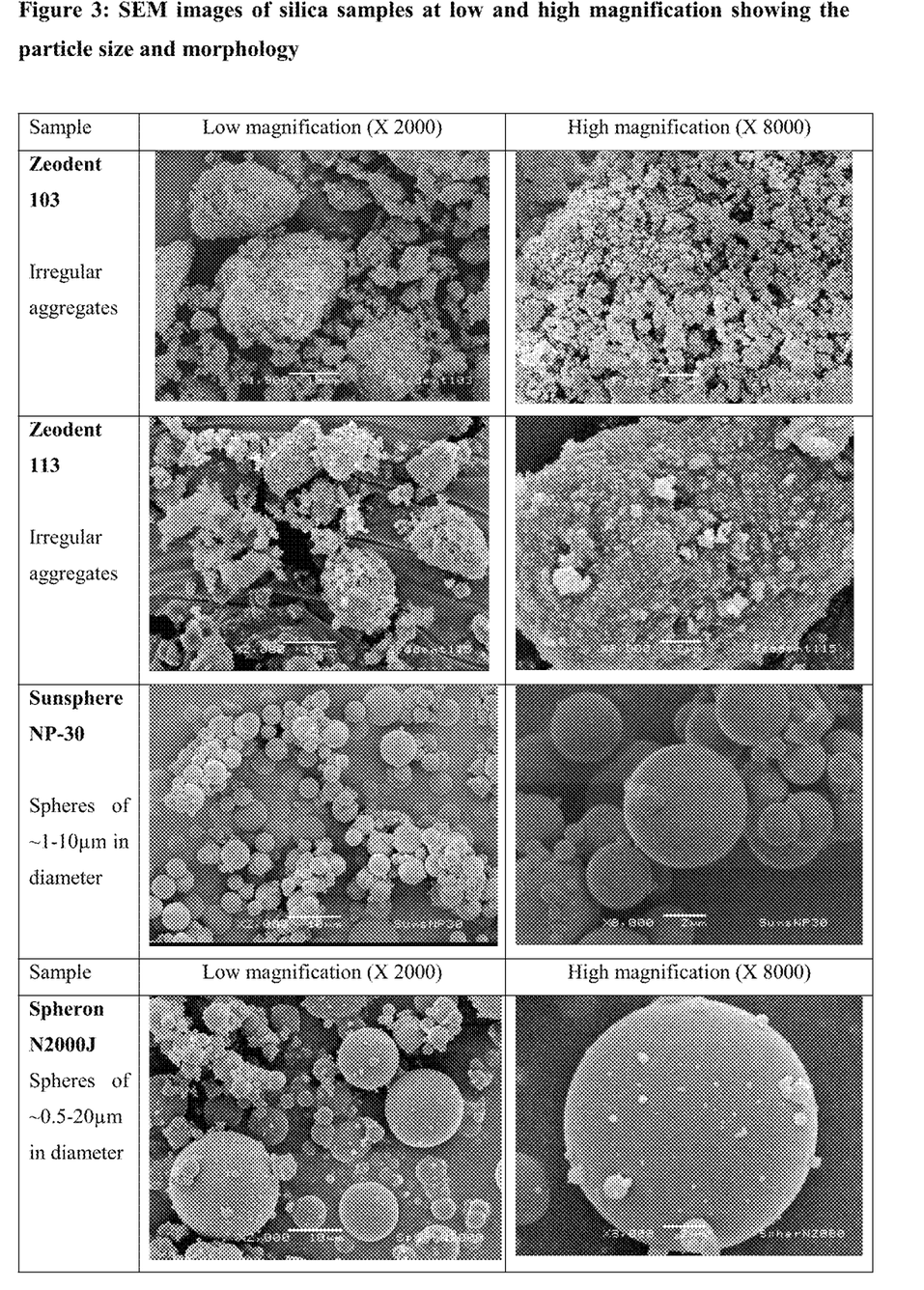
FIG. 3: SEM images of silica samples at low and high magnification showing particle size and morphology.
Figure 4A:
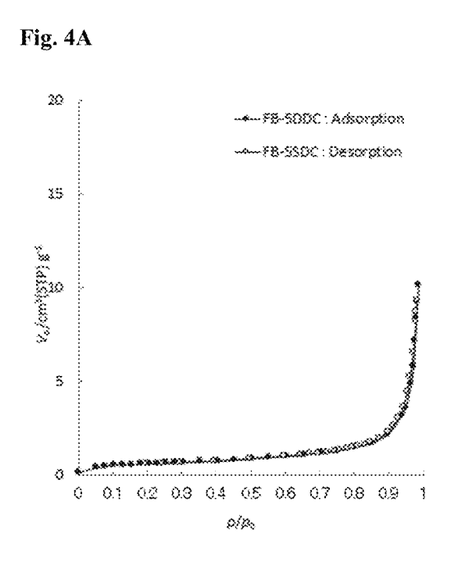
FIGS. 4A-4E: Adsorption/Desorption Isotherms (by Belsorp-mini)
Figure 4B:
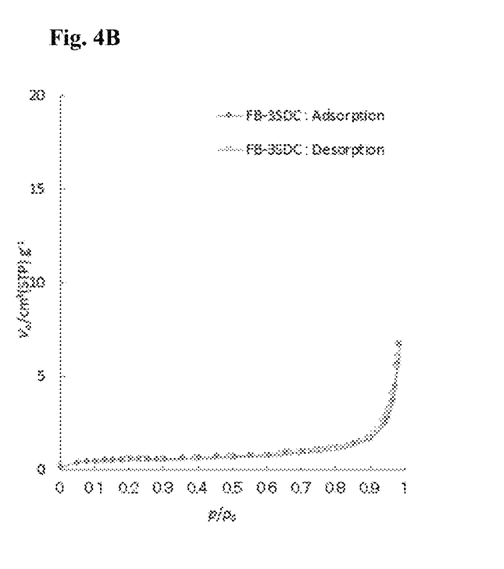
Figure 4C:
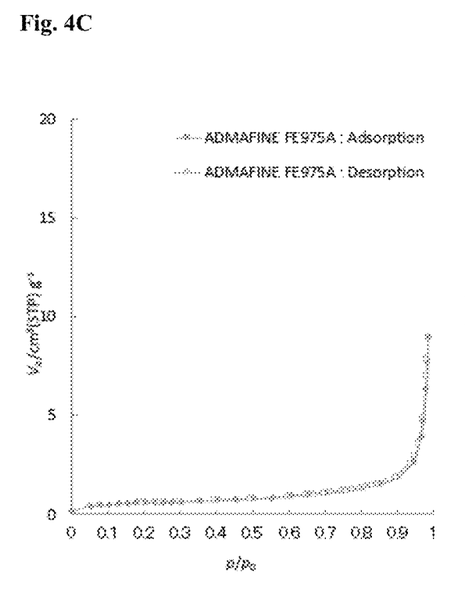
Figure 4D:
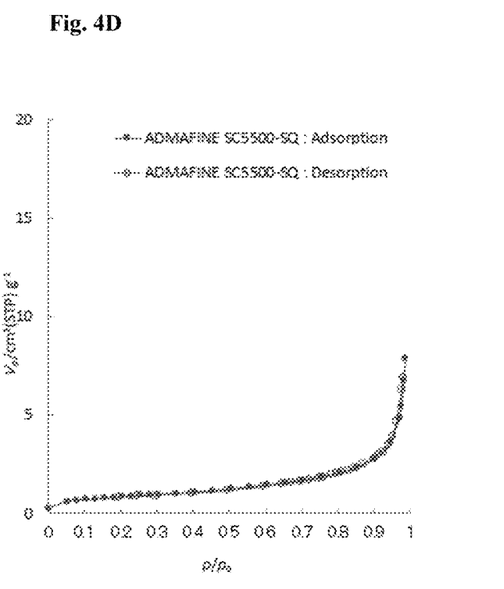
Figure 4E:
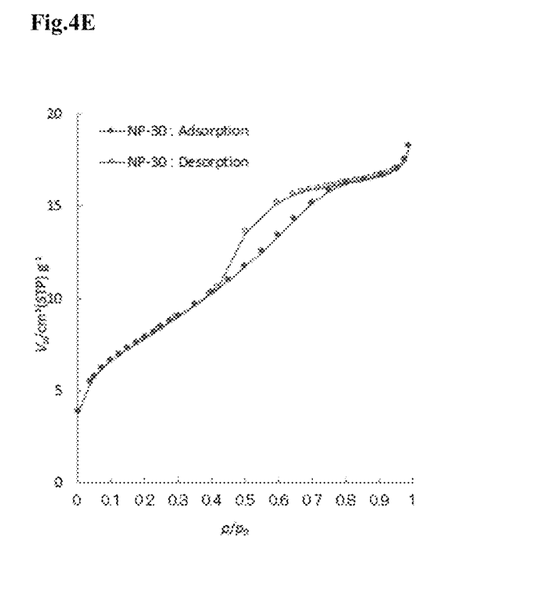
Figure 5A:
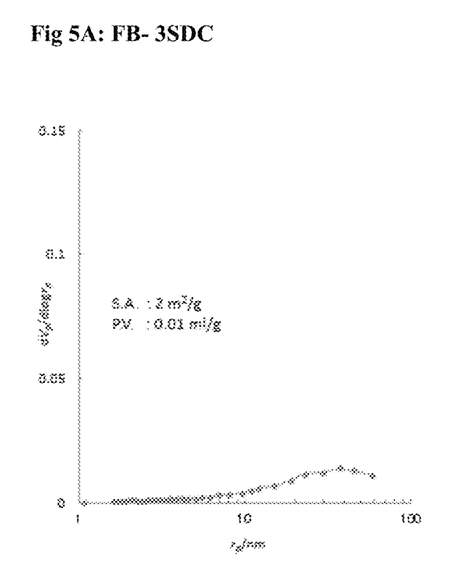
FIGS. 5A-5E: Pore Distribution (Desorption)
Figure 5B:
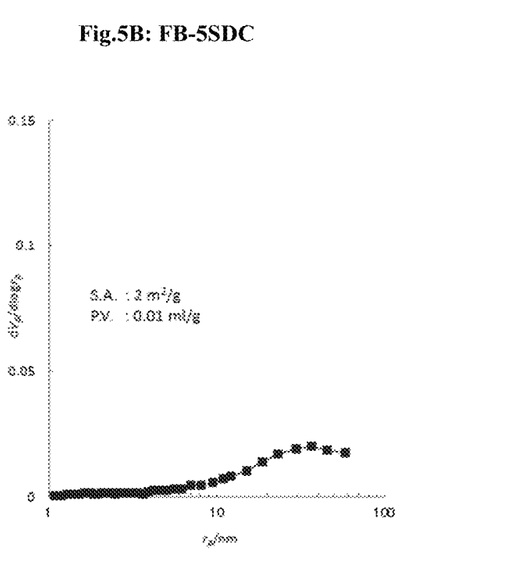
Figure 5C:
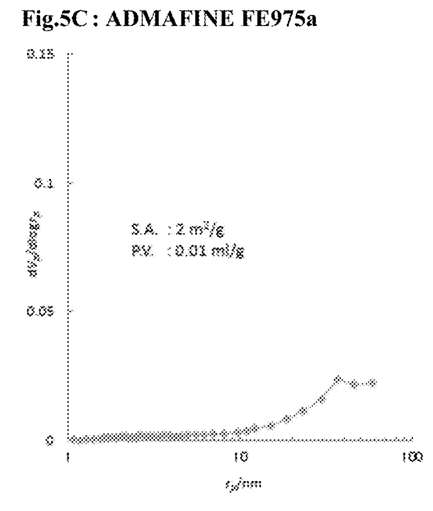
Figure 5D:
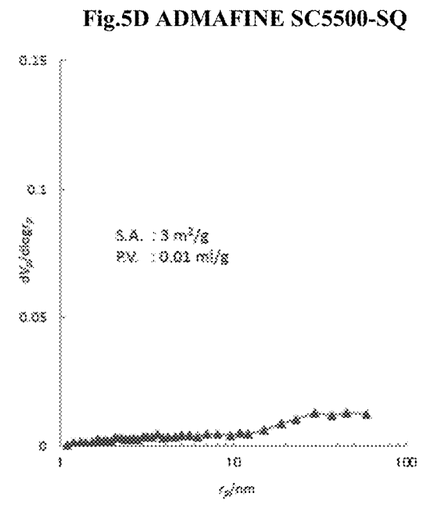
Figure 5E:
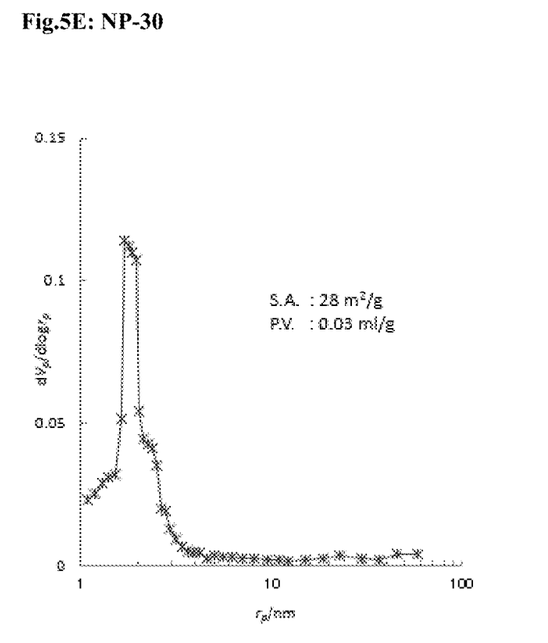

The silica gel particles of use in the invention comprise a high degree of sphericity i.e. they are spherical or substantially spherical, for example as can be seen by scanning electron micrography, for example as shown in Example 4 herein. For the avoidance of doubt, substantially spherical silica gel particle means any particle where the whole particle is mostly rounded or elliptical in shape. Suitably the silica gel particles of use in the invention comprise a smooth or a substantially smooth surface.

Suitably at least 90% of the spherical silica gel particles are substantially spherical, more suitably 95% of the spherical silica gel particles are essentially spherical, even more suitably 99% of the spherical silica gel particles are essentially spherical.

Suitably the silica gel particles of use in the invention have a mean particle diameter in the range from 1μ to 10μ, more suitably from 3μ to 8μ. Suitably the particles are generally of a uniform size and have a narrow particle size distribution for example from 1μ to 15μ. Particle size may be determined by laser diffraction.

Silica gel particles of use in the invention are anhydrous. The term "anhydrous" as used herein includes a very low amount of free and/or bound water present in the silica gel particles i.e. suitably 0.5 wt. % or less. In one embodiment the water content is less than 0.3 wt. %. In one embodiment the water content is less than 0.2 wt %. The amount of free and/or bound water may be determined by thermogravimetric (TGA) analysis. Analysis may be conducted on 20-30 mg samples using a TA-Instrument SDT Q600 simultaneous TGA/DSC, under air flow in the temperature range from ambient to 120° C., with a heating rate of 5° C./min, for example as demonstrated in Example 5 herein.

Suitably silica gel particles of use in the invention comprise a low amount of surface bound hydroxyl groups. Suitably the amount of surface bound hydroxyl groups present in the silica gel particles is less than 0.1% and more suitably is 0.0%. The amount of surface bound hydroxyl groups may be determined by thermogravimetric (TGA) analysis. Analysis may be conducted on 20-30 mg samples using a TA-Instrument SDT Q600 simultaneous TGA/DSC, under air flow in the temperature range from 120° C. to 1000° C., with a heating rate of 5° C./min, for example as demonstrated in Example 5 herein.

The silica gel particles of use in the invention are amorphous or essentially amorphous i.e. with no crystalline material(s) detectable as determined by X-ray diffraction measurements.

Silica gel particles of use in the invention comprise a low pore volume as compared to other known silica gel particles. Suitably the pore volume (ml/g) is less than 0.1, i.e. the pore volume (ml/g) is above zero but less than 0.1, for example in the range from 0.01 to 0.09 or from 0.01 to 0.08 or from 0.03 to 0.07.

In one embodiment according to the invention silica gel particles of use in the invention are non-porous or virtually non-porous i.e. comprise a substantially or completely closed surface (beyond the limit of detection). Porosity may be determined by the method described by Ojeda, Phys. Chem. Chem. Phys 5, 1859-1866, 2003 or as described in Examples 6 and 7 herein.

Suitably silica gel particles of use in the invention are relatively hard materials as compared to other precipitated silicas; as such they are more resistant to shearing stress and disintegrate less easily under shear. Suitably the compression strength (MPa) of a silica gel of use in the invention is in the range from 1800 to 2000, such as from 1850 to 1950. Compression strength may be determined by using a microcompressive strength tester.

Suitably the silica gel particles of use in the invention have smaller BET surface area values as compared to those observed for known dental abrasives such as the precipitated silicas available commercially as Zeodent-103 and Zeodent-115. The silica gel particles of use in the invention have a BET surface area ($m^2$/g) of 50 or less. In one embodiment the silica gel particles have a BET surface area ($m^2$/g) of 40 or less. In one embodiment the silica gel particles have a BET surface area ($m^2$/g) of 30 or less. In one embodiment the silica gel particles have a BET surface area ($m^2$/g) of 20 or less. In one embodiment the silica gel particles have a BET surface area ($m^2$/g) of 10 or less. In one embodiment the silica gel particles have a BET surface area ($m^2$/g) of 5 or less. BET surface area measurements are determined by measuring the amount of nitrogen adsorbed on a surface, suitably as described in Brunaur et al., J. Am. Chem. Soc., 60, 309 (1938) or as demonstrated in Examples 6 and 7 herein.

Suitably silica gel particles of use in the invention have a low oil absorption capacity as compared to those observed for known dental abrasives such as Zeodent-109 and Zeodent-119, reported to have oil absorption values (ml/100 g) of 79.8 and 110.7 respectively and as reported in WO2010/068433. The silica gel particles of use in the invention have an oil absorption capacity (ml/100 g) suitably of 20 to 50, more suitably of 35 or less, even more suitably in the range 25 to 35. Oil absorption may be measured according to the method described in U.S. Patent Application 2007/0001037A1, published 4 Jan. 2007.

Suitably the silica gel particles of use in the invention may be present in an amount from 0.1% to 15% by weight of the composition. In one embodiment the silica gel particles are present in an amount from 0.2% to 10% by weight of the composition. In one embodiment the silica gel particles are present in an amount ranging from 0.3% to 8% by weight of the composition. In one embodiment the silica gel particles are present in an amount up to 1% by weight of the composition for example ranging from 0.1% to 1%, such as from 0.2% to 0.7% by weight of the composition, such as about 0.5% by weight of the composition. In one embodiment the silica gel particles are present in an amount up to 10% by weight of the composition for example ranging from 0.1% to 10%, such as 2% to 8% by weight of the composition, such as about 5% by weight of the composition.

A dentifrice composition according to the invention may optionally further comprise a supplementary abrasive agent, provided that such agent does not significantly adversely impact on dentine abrasion.

Suitable examples of supplementary abrasive agents for use in the present invention include silica including fused silica, precipitated silica, hydrated silica, rice hull silica, aluminium silicate, alumina, hydrated alumina, calcined alumina, calcium carbonate, anhydrous dicalcium phosphate, dicalcium phosphate dihydrate, water-insoluble sodium metaphosphate, zirconia, perlite, diamond, pyrophosphates, pumice, polymer particles, calcium phosphate based minerals (e.g. tricalcium phosphate (TCP), hydrated HA and mixed phase (HA:TCP) calcium phosphate mineral) and mixtures thereof.

A supplementary abrasive agent may be used generally in an amount ranging from 0.1% to 20% by weight of the composition or from 0.1% to 10% by weight of the total dentifrice composition.

In one embodiment the dentifrice composition of the present invention is free of a fused silica.

In one embodiment the dentifrice composition of the present invention comprises silica gel particles as described herein as the sole abrasive agent.

Radioactive dentine abrasion (RDA) is a measure of the abrasiveness of a dentifrice. The established method for determining the abrasivity of a dentifrice formulation is by measuring the Relative Dentine Abrasivity (RDA) (Hefferen, B. A laboratory method for measuring dentifrice abrasivity. J. Dent. Res. 55 563-573, 1976 or as described in Example 3 herein). This assay measures loss of dentine due to extended brushing with a 25:40 w/w slurry of test material, e.g. toothpaste, from prepared samples of human dentine. The dentine samples are irradiated to generate $^{32}$P in the mineral. The assay measures radioactivity in the supernatant after brushing, relative to radioactivity liberated by brushing with a standard slurry of calcium pyrophosphate.

Suitably a composition of the present invention comprises an RDA value ranging from 10 to 250, for example in the range from 20 to 200 or from 30 to 150.

In one embodiment wherein the silica gel particles present in an amount ranging from 0.1% to 10% by weight of the composition, the RDA of the composition is in the range from 100 to 200.

In one embodiment wherein the silica gel particles are present in an amount ranging from 0.1% to 7% by weight of the composition, the RDA of the composition is in the range of from 100 to 140.

In one embodiment wherein the silica gel particles are present in an amount ranging from 0.1% to 1% by weight of the composition, the RDA of the composition is in the range from 10 to 100.

In one embodiment wherein the silica gel particles are present in an amount ranging from 0.3% to 0.7% by weight of the composition, the RDA of the composition is in the range of from 20 to 60.

The cleaning ability of dentifrices may be demonstrated by using the Pellicle Cleaning Ratio (PCR) test—a laboratory method accepted as useful in the characterization of stain cleaning (whitening) actions of abrasive-containing dentifrices, for example as described in Example 2 herein. The PCR value is calculated relative to a standard material ($Ca_2P_2O_7$, Odontex Inc.) which is given the empirical value of 100.

Suitably a dentifrice according to the present invention comprises a PCR value ranging from 50 to 200, suitably in the range from 60 to 150.

In one embodiment wherein the silica gel particles are present in an amount ranging from 0.1% to 10% by weight, the PCR of the composition is in the range from 50 to 200.

In one embodiment wherein the silica gel particles are present in an amount ranging from 0.1% to 7% by weight of the composition, the PCR of the composition is in the range from 50 to 150.

In one embodiment wherein the silica gel particles are present in an amount ranging from 0.1% to 1% of the composition, the PCR of the composition is in the range from 50 to 110.

In one embodiment wherein the silica gel particles are present in an amount ranging from 0.3% to 0.7% by weight of the composition, the PCR of the composition is in the range of from 80 to 100.

A dentifrice according to the present invention shows excellent cleaning and stain removal of the tooth surface with minimal dentine abrasion. The high cleaning/low abrasivity properties of a dentifrice according to the invention may also be reflected in the Cleaning Efficiency Index value for the dentifrice. The Cleaning Efficiency Index value can be readily determined by one skilled in the art. See Schemehorn B R, Ball T L, Henry G M, Stookey G K. "Comparing dentifrice abrasive systems with regard to abrasion and cleaning." J. Dent Res 1992; 71: 559 or for example as described in Example 3 herein.

Suitably a dentifrice according to the present invention comprises a CEI value ranging from 1 to 3, suitably in the range from 1.2 to 2.5 or from 1.5 to 2.0.

Radioactive enamel abrasion (REA) is another measure of the abrasiveness of a dentifrice. The established method for determining the abrasivity of a dentifrice formulation is by measuring the Relative Enamel Abrasivity (REA) (Hefferen, J J. A laboratory method for measuring dentifrice abrasivity. J. Dent. Res. 55 563-573, 1976). This assay measures loss of enamel due to extended brushing with a 25:40 w/w slurry of test material, e.g. toothpaste, from prepared samples of human enamel. The enamel samples are irradiated to generate $^{32}P$ in the mineral. The assay measures radioactivity in the supernatant after brushing, relative to radioactivity liberated by brushing with a standard slurry of calcium pyrophosphate.

Suitably a dentifrice according to the present invention comprises an REA value of 15 or below, preferably an REA value of 10 or below, where the maximum safe and allowable REA value is 40.

A dentifrice composition of the present invention provides good cleaning with low abrasivity, resulting in cleaner, whiter and highly polished tooth surfaces, with less or no staining, reduced plaque and tartar resulting in improved oral health.

A dentifrice composition of the present invention may be aqueous or non-aqueous. Water employed in the preparation of commercially suitable compositions should preferably be of low ion content and free of organic impurities. When present water will generally comprise from about 5% to about 70% such as from 10% to 50% by weight of the composition. Generally the level of water is up to 40%, such as up to 20%, such as from 0.1% to 15% by weight of the composition. The amount of water includes free water which is added plus that which is introduced with other materials, such as with humectants or surfactants.

A dentifrice composition of the present invention may further comprise a water-soluble condensed phosphate salt, such as an alkali metal pyrophosphate, tripolyphosphate or higher polyphosphate salt, in particular a water-soluble alkali metal tripolyphosphate salt. Suitably the sodium form of this salt is preferred, although the potassium or mixed sodium and potassium salts could be used as a preferred embodiment as well. All physical forms can be used, e.g. a hydrate or a dehydrated form.

Most suitably the water-soluble alkali metal tripolyphosphate salt is sodium tripolyphosphate.

Suitably the water soluble condensed phosphate salt (such as an alkali metal tripolyphosphate salt) is present in an amount from 1.0% to 20.0%, for example from 2.0% to 15.0%, or 1.0% to 10%, or 5.0% to 10.0% by weight of the composition.

A dentifrice composition of the present invention may further comprise an alkali metal bicarbonate salt. The inclusion of such a salt in a dentifrice composition is beneficial for several reasons such as for providing good plaque removing capabilities, as well as for improving the whitening properties of dentifrices. Importantly bicarbonate salts provide a clean fresh feeling in the oral cavity after brushing and rinsing with water. Suitably the alkali bicarbonate is sodium bicarbonate. Suitably the sodium bicarbonate is present in an amount from 20% to 90% by weight of the composition, preferably from 60% to 80% by weight of the composition, more preferably from 65% to 70% by weight of the composition e.g. from 66% to 68% by weight of the composition.

A dentifrice composition of the present invention may comprise one or more active agents conventionally used in dentifrice compositions, for example, a fluoride source, a desensitising agent, an anti-bacterial agent, an anti-plaque agent, an anti-calculus agent, an oral malodour agent, an anti-inflammatory agent, an anti-oxidant, an anti-fungal agent, a wound healing agent or a mixture of at least two thereof. Such agents may be included at levels to provide the desired therapeutic effect.

Examples of desensitising agents include a tubule blocking agent or a nerve desensitising agent and mixtures thereof, for example as described in WO02/15809 (Block). Examples of desensitising agents include a strontium salt such as strontium chloride, strontium acetate or strontium nitrate or a potassium salt such as potassium citrate, potassium chloride, potassium bicarbonate, potassium gluconate and especially potassium nitrate.

A desensitising agent such as a potassium salt is generally present in an amount ranging from 2% to 8% by weight of the composition, for example 5% by weight of the composition.

In another embodiment the desensitising agent comprises an arginine calcium carbonate salt. Suitably the arginine salt is present in an amount ranging from 0.5% to 30% by weight of the composition, such as from 1% to 10% by weight of the composition or from 1% to 10% by weight of the composition such as from 2% to 8% by weight of the composition.

In one embodiment the desensitising agent comprises a bioactive glass. Suitably the bioactive glass consists of 45% by weight silicon dioxide, 24.5% by weight sodium oxide, 6% by weight phosphorus oxide, and 24.5% by weight calcium oxide. One such bioactive glass is available commercially under the trade name, NOVAMIN, also known as 45S5 BIOGLASS.

Suitably the bioactive glass is present in an amount ranging from 1% to 20% by weight of the composition, such as from 1% to 15% by weight of the composition, or from 1% to 10% by weight of the composition, or from 2% to 8% by weight of the composition.

In one embodiment the desensitising agent comprises a stannous salt such as stannous chloride or stannous fluoride. Stannous salts, through hydrolysis and oxidation reactions, form insoluble metal salts that precipitate in dentinal tubules and on the dentine surface to provide effective relief from dentine hypersensitivity. Stannous salts also provide a benefit against dental erosion, dental caries and plaque/gingivitis.

In a further embodiment the desensitising agent includes silica, colloidal silica, nano zinc oxide, sub-micron alumina and sub-micron polymer beads, in a fine particulate form comprising an average particle size in the range from 1 nm to 5µ.

Suitable sources of fluoride ions for use in the compositions of the present invention include an alkali metal fluoride such as sodium fluoride, an alkali metal monofluorophosphate such a sodium monofluorophosphate, stannous fluoride, or an amine fluoride in an amount to provide from 25 to 3500 ppm of fluoride ions, preferably from 100 to 1500 ppm. A typical fluoride source is sodium fluoride, for example the composition may contain 0.1 to 0.5% by weight of sodium fluoride, e.g. 0.204% by weight (equating to 923 ppm of fluoride ions), 0.2542% by weight (equating to 1150 ppm of fluoride ions) or 0.315% by weight (equating to 1426 ppm of fluoride ions).

Such fluoride ions help promote the remineralisation of teeth and can increase the acid resistance of dental hard tissues for combating caries, dental erosion (i.e. acid wear) and/or tooth wear.

Compositions of the present invention will contain additional formulating agents such as, surfactants, humectants, non-abrasive (thickening) silicas, flavouring agents, sweetening agents, opacifying or colouring agents, preservatives and water, selected from those conventionally used in the oral hygiene composition art for such purposes.

Suitable surfactants for use in the present invention include anionic surfactants such as a sodium $C_{10-18}$alkyl sulphate, e.g. sodium lauryl sulphate. Sodium lauryl sulphate is generally considered to be anionic and strongly charged and is useful if high levels of foaming are desired when brushing teeth.

In addition to anionic surfactants, zwitterionic, amphoteric, cationic and non- or low-ionic surfactants may be used to aid foaming characteristics. When anionic and amphoteric surfactants are used together an optimised foaming system is achieved that will provide both improved mouth feel and good cleaning. Examples of amphoteric surfactants include long chain alkyl (e.g. $C_{10}$-$C_{18}$ alkyl) betaines, such as the product marketed under the trade name 'Empigen BB' by Albright & Wilson and long chain alkyl amidoalkyl betaines such as cocamidopropylbetaine.

A particularly preferred example of an anionic/amphoteric surfactant combination for use in the present invention is sodium lauryl sulphate/cocamidopropylbetaine.

Suitably, the surfactant is present in the range from 0.1 to 15% by weight of the composition, for example from 0.5% to 10% by weight of the composition or from 1.0 to 5% by weight of the composition.

Suitable humectants for use in compositions of the invention include glycerin, xylitol, sorbitol, propylene glycol or polyethylene glycol, or mixtures of at least two thereof; which humectant may be present in an amount ranging from 10% to 80% by weight of the composition, for example from 20% to 70% by weight of the composition, or from 30% to 60% by weight of the composition.

It will be understood that compositions of the present invention may also be used outside the oral cavity, for the cleaning of dentures and the like.

The dentifrice compositions of the present invention are typically formulated in the form of toothpastes, instant powders, tablets and gels. Preferred compositions of the present invention are toothpastes and gels.

The dentifrices of the present invention are typically formulated in the form of a paste that is suitable for containing in and dispensing from a laminate tube or a pump as conventionally used in the art. Additional examples may include bag-in-can or bag-on-valve delivery systems that utilise a foaming agent such as pentane or iso-pentane.

A typical process for making the composition of this invention involves admixing the ingredients, suitably under a vacuum, until a homogeneous mixture is obtained, and adjusting the pH if necessary The present invention provides a composition as hereinbefore defined for use in reducing stain, plaque and/or tartar on a dental surface.

The present invention provides a method of reducing stain, plaque and/or tartar on a dental surface which comprises applying an effective amount of a composition as hereinbefore defined to an individual in need thereof. The invention is further illustrated by the following examples.

Example 1: Compositions of the Invention

TABLE 1

|  | Dentifrice Formulation | |
| --- | --- | --- |
| Raw Material | Formulation 1 % w/w | Formulation 2 % w/w |
| Sorbitol 70% solution - humectant | 30.000 | 30.000 |
| Sunsphere NP-30 | 0.500 | 5.000 |
| Zeodent 153 - thickening silica | 12.000 | 12.000 |
| Glycerin - humectant | 8.000 | 8.000 |
| Polyethylene glycol - humectant | 3.000 | 3.000 |
| Cocoamidopropylbetaine - surfactant | 1.200 | 1.200 |
| Xanthan gum - thickener | 0.800 | 0.800 |
| Titanium dioxide - opacifier | 0.100 | 0.100 |
| Potassium Nitrate - active | 5.000 | 5.000 |
| Sodium Fluoride - active | 0.315 | 0.315 |
| Flavour oil | 1.200 | 1.200 |
| Saccharin sodium - sweetener | 0.350 | 0.350 |
| Sodium Hydroxide - pH adjuster | 0.010 | 0.010 |
| Water | To 100 | To 100 |

Example 2: Pellicle Cleaning Ratio Test (PCR) as a Measure of Stained Pellicle Removal from Bovine Enamel Introduction Previous studies (J. Dent. Res., 61:1236, 1982) have indicated that the results of the in-vitro PCR test with dentifrice slurries may be considered to be predictive of clinical findings with a reasonable degree of confidence.

Dentifrice formulations 1 and 2 above were assessed for their ability to remove pellicle stain from bovine enamel and compared with similar comparative formulations (not encompassed within the scope of the invention) containing alternative silica abrasive materials. Formulation details of the Comparative Examples are shown in Table 2.

izing methacrylate resin so that only the enamel surfaces were exposed. The enamel surfaces were then smoothed on a lapidary wheel and polished with flour of pumice and water, then sonicated to remove excess debris. They were then lightly etched (60 seconds in 0.12M HCl, 30 seconds in saturated $NaCO_3$ and 60 seconds in 1.0% phytic acid) to expedite stain accumulation and adherence. They were then placed on a rotating rod alternately exposing them to staining broth containing gastric mucin as a protein source and coffee, tea and $FeCl_3 \cdot 6H_2O$ as staining sources (i.e., 1.35 g coffee, 1.35 g tea, 0.02 g Fe and 1.0 g mucin in 400 ml) for a minimum of 10 days to ensure the specimens developed sufficient stain.

The amount of in vitro stain was graded photometrically (Minolta 2600d, colorimeter) using only the L value of the LAB scale. The area of the specimens measured was a ¼ inch diameter circle in the centre of the enamel sample. Specimens with L value measurements between 30-38 (30 being more darkly stained) were used. On the basis of these measurements, the specimens were divided into groups of 16 specimens each, with each group having the same average baseline measurement.

The specimens were then mounted on a mechanical V-8 cross-brushing machine equipped with soft nylon-filament (Oral-B 40 Indicator) toothbrushes. Toothbrushes were conditioned by running the brushing machine for 1,000 strokes in deionised water. Tension on the enamel surface was adjusted to 150 g. The dentifrices were used as slurries prepared by mixing 25 g of dentifrice with 40 ml of deionised water. The ADA reference material was prepared by mixing 10 g of material and 50 ml of a 0.5% CMC solution. The specimens were brushed for 800 double strokes. To minimise mechanical variables, one specimen per group was brushed on each of the eight brushing heads. Fresh slurries were used for each specimen brushed. Following brushing, specimens were rinsed, blotted dry, and measured again for stain as previously described.

TABLE 2

| | Dentifrice Formulation | | | | | | |
| --- | --- | --- | --- | --- | --- | --- | --- |
| | Comparative Formulation (A) | Comparative Formulation (B) | Comparative Formulation (C) | Comparative Formulation (D) | Comparative Formulation (E) | Comparative Formulation (F) | Comparative Formulation (G) |
| | Silica type (abrasive) | | | | | | |
| Raw Material | Precipitated silica % w/w | Precipitated silica Zeodent113 % w/w | Precipitated silica Zeodent103 % w/w | Fused silica Spheron P-1500 % w/w | Fused silica Spheron N2000J % w/w | Fused silica Teco-Sil 44CSS % w/w | Fused silica Teco-Sil 44C % w/w |
| Sorbitol 70% solution | 30.000 | 30.000 | 30.000 | 30.000 | 30.000 | 30.000 | 30.000 |
| Abrasive silica | 6.000 | 5.000 | 5.000 | 5.000 | 5.000 | 5.000 | 5.000 |
| Thickening silica | 12.000 | 12.000 | 12.000 | 12.000 | 12.000 | 12.000 | 12.000 |
| Glycerin | 8.000 | 8.000 | 8.000 | 8.000 | 8.000 | 8.000 | 8.000 |
| Polyethylene glycol | 3.000 | 3.000 | 3.000 | 3.000 | 3.000 | 3.000 | 3.000 |
| Cocoamidopropylbetaine | 1.200 | 1.200 | 1.200 | 1.200 | 1.200 | 1.200 | 1.200 |
| Xanthan gum | 0.800 | 0.800 | 0.800 | 0.800 | 0.800 | 0.800 | 0.800 |
| Titanium dioxide | 0.100 | 0.100 | 0.100 | 0.100 | 0.100 | 0.100 | 0.100 |
| Potassium Nitrate | 5.000 | 5.000 | 5.000 | 5.000 | 5.000 | 5.000 | 5.000 |
| Sodium Fluoride | 0.315 | 0.315 | 0.315 | 0.315 | 0.315 | 0.315 | 0.315 |
| Flavour oil | 1.100 | 1.200 | 1.200 | 1.200 | 1.200 | 1.200 | 1.200 |
| Saccharin sodium | 0.350 | 0.350 | 0.350 | 0.350 | 0.350 | 0.350 | 0.350 |
| Sodium Hydroxide | 0.010 | 0.010 | 0.010 | 0.010 | 0.010 | 0.010 | 0.010 |
| Water | To 100 | To 100 | To 100 | To 100 | To 100 | To 100 | To 100 |

Methodology

Bovine, permanent, central incisors were cut to obtain labial enamel specimens approximately 8×8 mm². The enamel specimens were then embedded in an autopolymer- The difference between the pre- and post-brushing stain measurements was determined and the mean and standard error calculated for the reference group. The cleaning ratio for the reference material group was assigned a value of 100.

The mean decrement for the reference group was divided into 100 to obtain a constant value to multiple times each individual test decrement within the study. The individual cleaning ratio of each specimen was then calculated (decrement X constant). The mean and standard error mean (SEM) for each group (N=16) was then calculated using the individual cleaning ratios. The larger the value of the cleaning ratio, the greater the amount of stained pellicle removed.

Statistical analyses of the individual means were performed with a one-way analysis of variance (ANOVA) model using Sigma Stat (3.1) Software. Since the ANOVA indicates significant differences, the individual means were analysed by the Student Newman-Keuls (SNK) test.

Results

Figure 1:
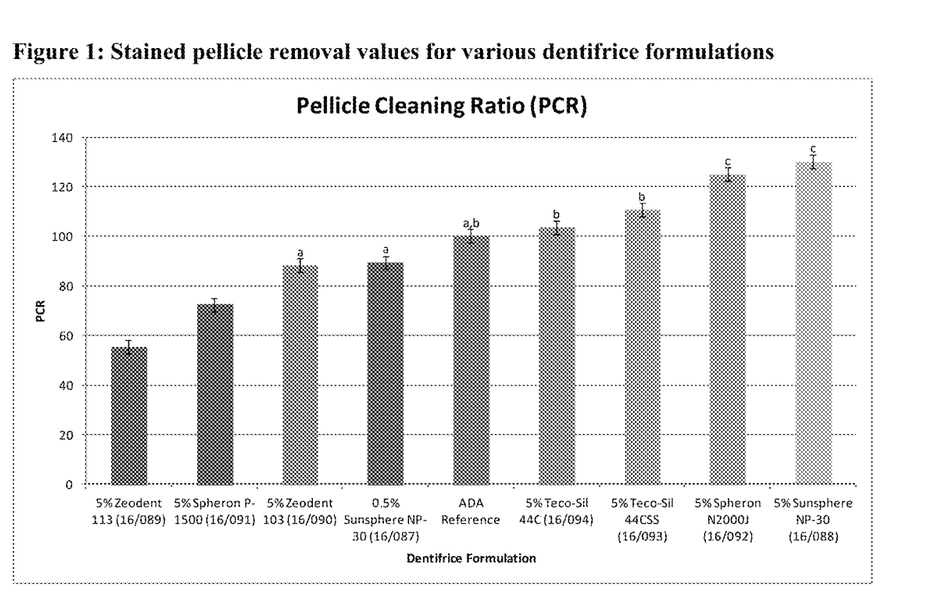
FIG. 1: Stained pellicle removal values for various dentifrice formulations.

The results are shown graphically in FIG. 1.

The error bars represent SEMs. Values connected by letters a, b or c do not differ significantly (p>0.05) as determined by Student Newman-Keuls analysis.

The silica gel particles of use in the invention were the most effective in removing stain from pellicle. One of the fused silicas tested, Comparative Example E (Spheron N2000J), gave similar results, but, directionally, the results from the formulation containing the silica gel of use in the invention gave the best results. The silica gel of use in the invention, cleaned, as effectively at a ten-fold lower concentration, as a precipitated silica tested (Zeodent 103) and significantly more effectively than another precipitated silica (Zeodent 113) and a fused silica (Spheron P-1500).

Example 3: Relative Dentine Abrasivity Test (RDA) as a Measure of Abrasivity on Bovine Enamel Samples Introduction Dentifrice formulations 1 and 2 above were assessed for their abrasivity (as determined by RDA) and compared as against similar comparative formulations (not encompassed within the scope of the invention) having alternative silica abrasive materials.

Methodology

The procedure used was the ISO/ADA recommended procedure for determination of dentifrice abrasivity. The dentin specimens (8) were placed in a neutron flux under the controlled conditions outlined by the ISO/ADA. The specimens were then mounted in methyl methacrylate so they would fit in a V-8 cross-brushing machine. The specimens were brushed for 1,500 strokes in a precondition run (since the teeth had been used previously) using a slurry consisting of 10 g ISO/ADA reference material in 50 ml of a 0.5% CMC glycerin solution. The brushes used were those specified by the ISO/ADA and had been used in a previous study. The brush tension was 150 g. Following the precondition run, the test was performed using 150 g and 1,500 strokes in a sandwich design in which each test material slurry (25 g dentifrice/40 ml water) was flanked by the reference material slurries (10 g ADA reference/50 ml 0.5% CMC) as outlined below in Table 3:

TABLE 3

Sandwich brushing design of RDA testing of dentifrice formulations and ADA reference material slurries

| Run | Slurry |
| --- | --- |
| 1 | ADA Reference Material |
| 2 | 0.5% Sunsphere NP30 |

TABLE 3-continued

Sandwich brushing design of RDA testing of dentifrice formulations and ADA reference material slurries

| Run | Slurry |
| --- | --- |
| 3 | ADA Reference Material |
| 4 | 5% Sunsphere NP-30 |
| 5 | ADA Reference Material |
| 6 | 5% Zeodent 113* |
| 7 | ADA Reference Material |
| 8 | 5% Zeodent 103* |
| 9 | ADA Reference Material |
| 10 | 5% Spheron P-1500* |
| 11 | ADA Reference Material |
| 12 | 5% Spheron N2000J* |
| 13 | ADA Reference Material |
| 14 | 5% Teco-sil 44CSS* |
| 15 | ADA Reference Material |
| 16 | 5% Teco-sil 44C* |
| 17 | ADA Reference Material |

*included for comparative purposes

A 1 ml sample was removed from each reference material slurry, weighed (0.01 g) and added to 4.5 ml of scintillation cocktail. The samples were well mixed and immediately placed on the scintillation counter for radiation detection. Following counting, the net counts per minute (CPM) values were divided by the weight of the sample to calculate the net CPM/gram of slurry. The net CPM/g of the pre- and post-ADA reference material for each test slurry were then calculated and averaged to use in the calculation of the RDA for the test material. The ISO/ADA material was assigned a value of 100 and its ratio to the test material was calculated. Recently, a new lot of the ADA reference material has been used. This material is 3.6% less abrasive than old batches, thus requiring the addition of 3.6% to the reference material CPM. This allows the direct comparison of this data to previous data.

Statistical analyses were performed by a one-way ANOVA model using Sigma Stat Software (13.0). Since significant differences were indicated, the individual means were analysed by the Student Newman Keuls (SNK) test.

Results

Figure 2:
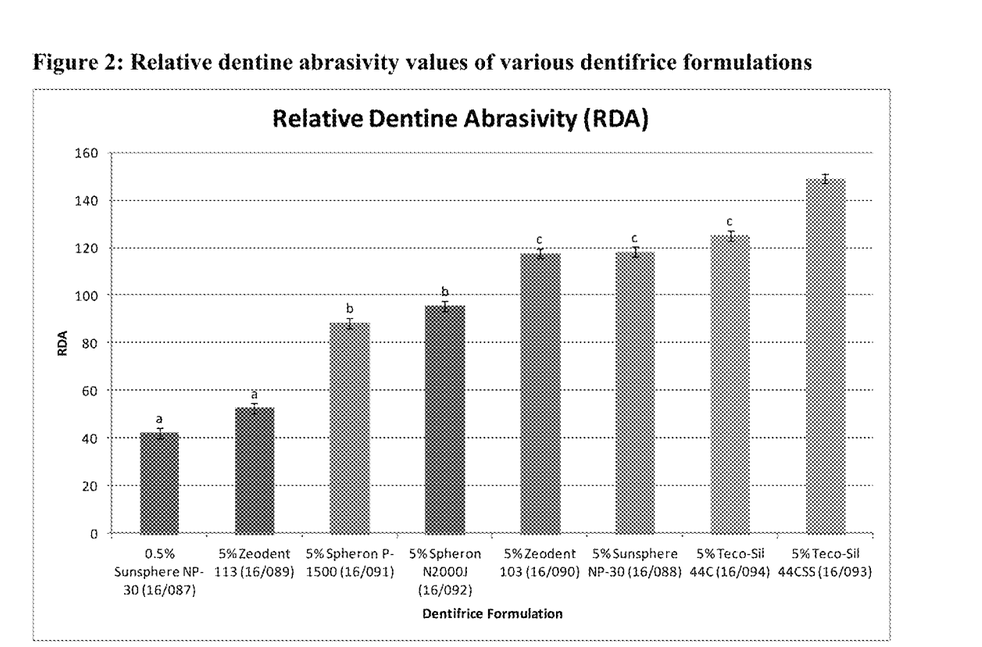
FIG. 2: Relative dentine abrasivity values of various dentifrice formulations.

The RDA results are shown graphically in FIG. 2. In addition, the mean, standard deviation (SD) and SEM for each group were calculated and also shown in FIG. 2.

The dentifrice containing 0.5% Sunsphere NP-30 silica and the dentifrice containing 5% of a precipitated silica (Zeodent 113) gave similar, low RDA values, which were significantly lower than all the other silica materials tested. The dentifrice containing 5.0% Sunsphere NP-30 silica had a similar RDA to another dentifrice containing 5% (of a different) precipitated silica (Zeodent 103). One of the fused silicas tested (Teco-Sil 44CSS) was significantly more abrasive than all the other dentifrices tested. All the dentifrices tested were within acceptable limits for products on the market today and met the ISO and ADA requirements.

The PCR and RDA data shown in FIGS. 1 and 2 are also shown in tabulated form in Table 4. The cleaning efficiency index (CEI) for each of the formulations tested (excluding SEM error values) are also shown. The CEI values were determined according to the following calculation $$CEI = (RDA + PCR - 50)/RDA$$

TABLE 4

| Dentifrice Formulation | RDA | PCR | CEI |
|---|---|---|---|
| 0.5% Sunsphere NP-30 | 42.23 ± 2.07 | 89.4 ± 4.4 | 1.93 |
| 5% Zeodent 113* | 52.58 ± 0.83 | 55.4 ± 2.7 | 1.10 |
| 5% Spheron P-1500* | 88.39 ± 4.71 | 72.4 ± 2.9 | 1.25 |
| 5% Spheron N2000J* | 95.57 ± 2.56 | 125.0 ± 3.8 | 1.78 |
| 5% Zeodent 103* | 117.59 ± 4.04 | 88.2 ± 2.9 | 1.32 |
| 5% Sunsphere NP-30 | 118.20 ± 4.29 | 130.1 ± 4.8 | 1.68 |
| 5% Teco-Sil 44C* | 125.16 ± 3.27 | 103.5 ± 3.8 | 1.43 |
| 5% Teco-Sil 44CSS* | 149.12 ± 5.72 | 110.6 ± 3.9 | 1.41 |

*included for comparative purposes

Example Four

Scanning Electron Microscopy (SEM) of silica samples was undertaken to determine the size and morphology of the particles. Fused silicas and precipitated silicas are included for comparative purposes.

Instrumentation

SEM of gold coated samples mounted on carbon pads on aluminium stubs was conducted on a Jeol 6480 LV SEM operating at 10 eV.

Results

SEM images of the silica samples are shown in FIG. 3.

Discussion

The Zeodent and Teco-Sil samples consisted of irregular aggregates of microdimension. Zeodent samples appeared to have nanoscale texture, the Teco-Sil materials were smoother and also exhibited some particles with plate-like morphology. Sunsphere NP-30 and Spheron materials consisted of essentially smooth, spherical particles. The Spheron P-1500 differed from the other spherical particles in that the surface was roughened due to nanometre sized projections on the surface.

Example Five

TGA-DSC was conducted on the powder samples by heating in air flow to 1000° C. to determine weight loss with increasing temperature and phase changes (if any).

Instrumentation

Analysis was conducted on 20-30 mg samples using a TA-Instruments SDT Q600 simultaneous TGA/DSC, under air flow in the temperature range from ambient to 1000° C. with a heating rate of 5° C. min$^{-1}$.

Results

The results are demonstrated in Table 5 below showing weight percent loss as measured by TGA over the range Room Temperature (RT) to 120° C. (mainly bound water) and 120° C. to 1000° C. (mainly bound hydroxyls) of the silica samples.

TABLE 5

| Sample | Wt % loss RT-120° C. | Wt % loss 120° C.-1000° C. |
|---|---|---|
| Zeodent 103* | 8.02 | 3.78 |
| Zeodent 115* | 8.03 | 3.04 |
| Sunsphere NP-30 | 0.19 | 0 |
| Spheron N-2000J* | 1.76 | 1.95 |
| Spheron P-1500* | 1.26 | 0.82 |
| Teco-Sil 44C* | 0.06 | 0 |
| Teco-Sil 44CSS* | 0.18 | 0.12 |

*included for comparative purposes

Example 6—Surface Area and Porosity Analysis

The surface areas of the silica samples were measured by BET $N_2$ adsorption, isotherm plots were also measured to determine the pore size and volume.

Instrumentation

Calculated Braun Emmet Teller (BET) specific surface areas from gas sorption ($N_2$, 77 K) were measured on Micromeritics 3-Flex gas sorption analyser. All powder samples (400-700 mg) were pre-degassed at 200° C. for 8 hours under vacuum ($10^{-3}$ mbar) in the oven and then degassed at 200° C. for 16 hours under dynamic high vacuum ($10^{-6}$ mbar) in the 3-Flex analyser prior to analysis.

Results

Surface Area

The surface area measurements are shown in Table 6, Zeodent 103 samples and Spheron P-1500 had moderate surface areas of 80-90 m$^2$/g and Zeodent 103 had a surface area of 45 m$^2$/g, the remaining samples had low surface areas.

Porosity

Isotherms plots of the $N_2$ adsorption desorption profiles at 77K and pore size distribution were measured and calculated by modern non-local density functional theory (NLDFT).[1] The measured surface areas and calculated porosity from isotherm measurement are shown in Table 6.

TABLE 6

Table of measured surface areas of the silica samples

| Sample | BET surface area (m$^2$ g$^{-1}$) | Correlation factor | Porosity |
|---|---|---|---|
| Zeodent-103* | 45.41 ± 0.5278 | 0.9994736 | Mesoporous (up to 500 Å) |
| Zeodent-115* | 80.51 ± 0.8539 | 0.9995594 | Mesoporous (up to 500 Å) |
| Sunsphere-NP-30 | 4.51 ± 0.1915 | 0.9985096 | Non-porous |
| Spheron-N-2000J* | 1.16 ± 0.0311 | 0.9989359 | Non-porous |
| Spheron-P-1500* | 89.50 ± 0.9652 | 0.9998312 | Mesoporous (<200 Å) |
| Teco-Sil-44C* | 2.74 ± 0.0453 | 0.9989531 | Virtually non-porous |
| Teco-Sil-44CSS* | 3.58 ± 0.0539 | 0.9991286 | Virtually non-porous |

*included for comparative purposes

Overall the order of decreasing surface area for the samples was found to be:

Spheron P-1500>Zeodent-115>Zeodent-103>Sunsphere NP-30>TecoSil 44CSS>TecoSil 44C>Spheron N-2000J Discussion The Zeodent and Spheron P-1500 samples were found to have moderately high surface area and mesoporosity, the remaining samples were essentially low surface area and non-porous.

Example 7—Specific Surface Area and Pore Volume

Device

BELSORP—mini (MicrotracBEL, Japan)

TABLE 7

| | Samples |
|---|---|
| Maker | Product (Lot) |
| Denka* | FB-3SDC (B7022101) |
| Denka* | FB-5SDC (B7041002) |

TABLE 7-continued

| Maker | Product (Lot) |
|---|---|
| Admatechs* | ADMAFINE FE975A |
| Admatechs* | ADMAFINE SC5500-SQ (DBH046) |
| AGSI | NP-30 (9176T30704) |

*spherical fused silica materials, included for comparative purposes

Principle

The specific surface area, pore volume, and pore diameter were determined using the nitrogen adsorption method. Prior to analysis, the silica sample was preconditioned to remove physically bonded impurities in degassing process which was accomplished by elevated temperature in conjunction with continuously flowing inert gas. The volume of gas adsorbed onto the silica surface was measured at the boiling point of nitrogen (−196° C.). The amount of adsorbed gas was correlated to the specific surface area of the silica particle. The calculation was based on the BET (Brunauer, Emmett and Teller) theory. Nitrogen adsorption method also enables the determination of pore volume and diameter. Measurements were carried out using the following protocols:

Measurement Conditions

Specific Surface Area

Preconditioning: Heating at 300° C. with $N_2$ flow 30 mL/min for 30 minutes. Cooling at room temperature and 30 minutes in $N_2$ Measurement of Nitrogen partial pressure: Multipoint measurement Pore Volume Preconditioning: Heating at 300° C. with $N_2$ flow 30 mL/min for 30 minutes. Cooling at room temperature and 30 minutes in $N_2$ flow Nitrogen pressure on measurement: 0.1 MPa Operating Procedure 1). Fill 0.2 g of sample to a sample tube and reduce the pressure to the region of measurement conditions.

2) Close a valve of the sample tube and weigh it (A).

3) Estimate weight difference between A and sample tube only (Blank).

4) Start the measurement of the porosity.

5) Specific surface area is calculated using next two equations.

$$\frac{P1}{V1(P0-P1)} = \frac{1}{VmC} + \frac{C-1}{VmC} \times \frac{P1}{P0} \quad \text{[BET equation]}$$

[Relational Calculus Between Specific Area and Vm]
Results

| Sample | FB-3SDC | FB-5SDC | FB975A | SC5500-SQ | NP30 |
|---|---|---|---|---|---|
| Surface Area [m²/g] | 2 | 2 | 2 | 3 | 28 |
| Pore volume [mL/g] | 0.01 | 0.01 | 0.01 | 0.01 | 0.03 |

The invention claimed is:

1. A dentifrice composition comprising non-fused spherical, anhydrous, amorphous, silica gel particles obtained by a process that involves precipitation followed by calcination to remove water to produce a dense particulate silica material, and wherein said silica gel particles comprise:
   a. a pore volume from 0.03 ml/g to less than 0.1 ml/g;
   b. a mean particle size from 1μ to 10μ;
   c. a BET surface area of 50 m²/g or less;
   d. an oil absorption capacity of 20 to 50 ml/100 g; and
   e. a water content of less than 0.2 wt. %.

2. A composition as claimed in claim 1 wherein the silica gel particles comprise a compression strength in the range 1800 MPa to 2000 MPa.

3. A composition as claimed in claim 1 wherein the silica gel particles are the sole abrasive in the dentifrice.

4. A composition as claimed in claim 1 comprising a supplementary abrasive.

5. A composition as claimed in claim 1 comprising a water soluble condensed phosphate.

6. A composition as claimed in claim 5 wherein the condensed phosphate is a water-soluble alkali metal tripolyphosphate salt.

7. A composition as claimed in claim 1 comprising a desensitizing agent.

8. A composition as claimed in claim 1 comprising a source of fluoride ions.

9. A dentifrice composition according to claim 1 wherein the silica gel particles comprise:
   a. a pore volume of 0.05 ml/g;
   b. a mean particle size of 4μ;
   c. a BET surface area of 40 m²/g; and
   d. an oil absorption capacity of 30 ml/100 g.

10. A Dentifrice composition according to claim 1 wherein the silica gel particles are present in an amount from 0.1% to 5% by weight of the composition.

11. A dentifrice composition according to claim 1 for use in cleaning, polishing and removing stains from the surface of the teeth or dentures.

* * * * *